United States Patent [19]
Bridges et al.

[11] Patent Number: 6,010,887
[45] Date of Patent: Jan. 4, 2000

[54] REGULATION OF GENE EXPRESSION

[75] Inventors: Ian George Bridges, Slater, Iowa; Simon William Jonathan Bright, Bucks, United Kingdom; Andrew James Greenland, Maidenhead, United Kingdom; Wolfgang Walter Schuch, Berks, United Kingdom; Andrew Merryweather, Loughbrough, United Kingdom; David Pioli, Limm, United Kingdom

[73] Assignees: Imperial Chemical Industries PLC, London; University of Leicester, Leicester, both of United Kingdom

[21] Appl. No.: 08/305,741

[22] Filed: Sep. 14, 1994

Related U.S. Application Data

[63] Continuation of application No. 08/025,803, Mar. 3, 1993, abandoned, which is a continuation of application No. 07/470,653, Jan. 26, 1990, abandoned.

[30] Foreign Application Priority Data

Jan. 26, 1989 [GB] United Kingdom .................. 8901676

[51] Int. Cl.[7] ........................... C12N 15/00; C12N 15/63; C12N 15/82; A01H 5/00
[52] U.S. Cl. ........................ 435/91.1; 435/440; 435/468; 435/320.1; 536/24.1; 800/278; 800/288; 800/295
[58] Field of Search .................. 435/69.1, 69.3, 435/91.1, 91.3, 177.1, 172.3, 320.1, 34, 38, 440, 468; 935/10, 16, 17, 34–36, 79, 83, 84; 800/278, 288, 295; 536/24.1

[56] References Cited

U.S. PATENT DOCUMENTS 5,096,815 3/1992 Ladner et al. .......................... 435/69.1

OTHER PUBLICATIONS

Miller, J. H. 1972, *Experiments in Molecular Genetics* Cold Spring Harbor Laboratory, cold Spring Harbor NY. pp. 146–152.
Lehming, N. et al. 1987. *Embo Journal*, vol. 6, pp. 3145–3153.
Gatz, C. et al. Molecular and General Genetics 277:229–237, 1991.

*Primary Examiner*—Mary E. Mosher
*Attorney, Agent, or Firm*—Pillsbury Madison & Sutro LLP

[57] ABSTRACT

Pseudo-operator sequences may be located in (or inserted into) plant genomes and utilized to drive expression of foreign genes. These pseudo-operator sequences are nucleotide sequences which are present at a suitable location in a gene at which repressor binding will lead to inhibition or enhancement of gene expression. The disclosed technique permits the design of altered specificity repressors, which bind the pseudo-operators.

14 Claims, 1 Drawing Sheet

| 434 REPRESSOR GENE | | SEQUENCE AT SalI SITE | |
|---|---|---|---|
| PRESENT | ABSENT | | |
| pPS1 | pAD18 | GTCGAACAAGAAAGTTTGTTCGAC | WILD-TYPE 434 $O_R1$ |
| pPS2 | pAD16 | GTCGAACAATATATATTGTTCGAC | "WILD-TYPE" SYNTHETIC |
| pPS3 | pAD17 | GTCGATCAATATATATTGATCGAC | "MUTANT" SYNTHETIC |
| pAD15.2 | pAD14 | G..................TCGAC | NO OPERATOR |

REGULATION OF GENE EXPRESSION

This is a continuation of application Ser. No. 08/025,803, filed on Mar. 3, 1993 now abandoned, which in turn is a continuation of application Ser. No. 07/470,653, filed Jan. 26, 1990, now abandoned.

This invention relates to the regulation of gene expression. More particularly, the invention is concerned with the regulation of plant gene expression by the use of bacterial repressor molecules. Specifically, the invention provides protocols and materials for the selection of repressors which have altered specificities.

Expression of a protein encoded by a gene is controlled by the interaction of certain regulatory proteins, known as DNA-binding proteins, with a region located upstream of the gene. Within the promoter region, there are located several operator regions which contains a specific oligonucleotide sequence to which these DNA-binding proteins specifically bind. These proteins can lead either to activation or repression of gene expression. Thus, they control the regulated expression of genes.

These DNA-binding proteins, which may in fact be either repressors or activators of gene expression, are hereinafter referred to for the sake of simplicity, as "repressors".

The repressor protein is encoded by a regulatory gene located elsewhere on the chromosome. The interaction of repressor and operator is affected by the presence or absence of particular chemical factors (inducers). Thus, in normal circumstances the repressor is expressed, thereby binding the operator and inhibiting expression of the gene, until a need for the particular protein encoded by the gene is indicated by the appearance in the environment of a specific inducer which interacts with the repressor to inhibit binding to the operator, thus allowing expression of the gene. For example, an enzyme which acts upon, say, a sugar molecule is not required unless that sugar is present and, therefore, in the absence of the sugar, the regulatory gene expresses the repressor which binds the gene operator and inhibits expression of the enzyme. The sugar itself acts as the inducer which then interacts with the repressor to prevent its binding to the operator thus allowing expression of the enzyme. Digestion of the sugar by the enzyme removes it from the environment allowing the repressor to return to its normal mode and act normally to inactivate enzyme expression. This mechanism can be viewed as a switching arrangement which switches gene expression on and off as dictated by the chemical content of the environment. Gene switching systems of the type described are best known in bacteria and many of the proteins and their target DNA binding sites are known in considerable detail. The repressor proteins usually bind as dimers to operators which exhibit a two-fold symmetry. The specificity of the repressor/promoter interaction is determined by the sequence specific interaction of specific amino acids of the repressor with the operator DNA. In some systems interactions have been subject to detailed biochemical analysis as well as high resolution X-ray crystallography. The best characterised class of DNA binding proteins exhibit a common helix-turn-helix motif with some degree of amino acid sequence homology. It is clear that the critical DNA binding domain of the repressor is contained within the helix-turn-helix region.

In eukaryotes it has been shown that control of gene expression is also regulated by the interaction of specific protein factors binding to DNA sequences close to the promoter region of genes. A number of factors have been isolated from yeast and mammalian cells and shown to interact with specific sequence motifs in a sequence-specific manner similar to bacterial systems. Characterisation of some of these factors has revealed a new "finger" motif which may be involved in the sequence specific binding of proteins.

In plants, the study of the control of gene regulation is lagging far behind. So far, only a few sequence elements[]have been identified in promoters which have been implicated in the binding of putative repressors. Recently, reports have been published on the preliminary identification of these repressors but none has been isolated and characterised.

It has been demonstrated that eukaryotic gene expression can be controlled through the use of bacterial repressor molecules in eukaryotic cells. In these experiments bacterial operator sequences have been inserted close to the promoters of mammalian genes. Cell lines gave been created which express the bacterial repressor. Control of expression of the target eukaryotic genes with operator insertions by repressor molecules has been demonstrated using transient expression assays. In these experiments not only repression of gene expression by the lac repressor has been demonstrated but also induction of gene expression, that is, relief of repression, using IPTG isopropyl thiogalactoside.

Thus, these experiments demonstrate that the detailed knowledge and manipulation of bacterial protein DNA/interactions can be used to control expression in mammalian cell cultures.

The application of such technologies could be further enhanced if the in vitro insertion of the operator sequences could be avoided. This could thus lead to the control of plant gene expression without the need to isolate and manipulate the said gene in vitro.

A clear understanding of the interactions involved in the recognition specificity and binding of 434 repressor to DNA sequences has recently emerged. The repressor binds as a dimer to a 14 base-pair operator that exhibits a high degree of dyad symmetry. Each monomer (Mr≡28000) consists of two globular domains linked by a short flexible stem. The carboxyl domain is responsible for contacts involved in dimerisation, whereas the amino domain is concerned with DNA binding, and contains the conserved helix-turn-helix structure (helices $\alpha 2$ and $\alpha 3$) also found in several other DNA-binding proteins.

Recognition of the operator sequence by 434 repressor is believed initially to involve weak non-specific interactions followed by "sliding" of the repressor along the DNA helix. X-ray crystallography of a repressor/operator complex has shown that the monomers are aligned such that the amino-terminus end of the $\alpha 3$ recognition helix is presented to the major groove of the DNA. Only when the correct specific contacts are made between the solvent-exposed amino acid side chains of the recognition helices and the functional groups of the DNA base-pairs can the repressor and operator move close enough together to allow the formation of strong ionic bonds between the peptide backbone and certain phosphates of the DNA backbone.

Formation of this tightly bound complex requires the slight underwinding of the major grooves containing the $\alpha 3$ helices and an overwinding of the minor groove, which corresponds to the central four base-pairs of the operator sequence. This correlates well with the observation that operators with A=T or T=A base-pairs at these central positions have a greater affinity for repressor, since the twisting of the DNA helix is energetically more favourable for A=T base-pairs.

Comparison of the 12 natural operator half-sites to which the 434 repressor binds reveals that the first three bases (ACA) are absolutely conserved and that an A at position 4 is present in all but one of the half-sites; the bases at other positions being more variable. X-ray crystallography suggests that it is these conserved base pairs that are specifically contacted by the amino acid side chains of the α3 helix: Gln28 interacts with the A at position 1, Gln29 with the G and T of the C≡G and A=T base-pairs at positions 2 and 3, and it is possible that Gln33 contacts the A and T of the T=A and A=T base-pairs at positions 4 and 5. Further evidence for the specificity of these contacts comes from the observation that repressors containing amino acid substitutions at positions 28 and 29 were all unable to bind wild-type operator. However, a mutant operator (5'-TCAATATATATTGA-3') was bound by repressor carrying a Gln28→Ala28 substitution. Studies on the effects of a Gln33→Ala33 substitution on operator binding further support the suggestion that Gln33 is involved in DNA sequence recognition.

The specificity of the contacts formed between repressor and operator can be exploited in order to construct repressors with altered DNA-binding specificities. Several studies, using 434cI, P22cI, lacI and trpR repressors, have shown that substitution of certain amino acids in the recognition helix will alter the DNA sequence bound by repressor. Although the molecular details of the interactions formed in some of these mutant repressor/pseudo-operator complexes are known, it is not yet possible to predict how a particular amino acid change will alter the DNA sequence recognition. Consequently, the isolation of an altered specificity repressor must involve a selection step in which the mutant repressor able to bind any given pseudo-operator may be identified from a pool in which the amino acids of the recognition helix have been randomly mutated.

An object of the present invention is to provide a means for controlling gene expression by repressors.

According to the present invention there is provided a method of regulating gene expression comprising locating within or inserting into a gene a pseudo-operator sequence, and providing a mutant regulatory gene encoding a repressor having an amino acid sequence which binds to the pseudo-operator.

Thus, the invention provides a method of inactivating a gene in a cell comprising locating, by DNA analysis, within the genome of the cell a pseudo-operator sequence and providing a mutant regulatory gene encoding a repressor having an amino acid sequence which binds to the located pseudo-operator.

The present invention further provides a method of isolating cells containing interacting repressor and operator genes comprising preparing a recombinant plasmid containing (1) the *Escherichia coli* lac operon, which includes the lacZ, lacY and lacA genes, and (2) a gene encoding a repressor protein, inserting said plasmid into a bacterial host and culturing same in the presence of ortho- or para-nitrophenyl-1-thio-β-galactoside, whereby the growth of cells in which expression of the lac gene is not repressed by the said repressor molecule is inhibited whereas the growth of cells in which repressor/operator binding occurs is not so inhibited, and recovering cells displaying non-inhibited growth characteristics.

Mutant repressors may be used or an exogenous potential pseudo-operator may be inserted within the operator region of the lac operon. The exogenous potential pseudo-operator is preferably of plant origin.

A convenient bacterial host is *Escherichia coli*.

Thus, the invention provides a means for altering the repressor of gene expression enabling genes to be inactivated. Pseudo-operators are DNA sequences which maintain the overall dyad symmetry of an operator but which contain different constituent bases. Computer analysis of known DNA sequences of the French bean GPAL2 gene among many others, and promoter and the mammalian c-myc genes, has revealed a number of possible pseudo-operators to different bacterial repressors.

[The plasmid pGAL2 has been deposited in *Escherichia coli* strain DH5 on Dec. 6, 1988 with the National Collection of Industrial and Marine Bacteria, Aberdeen, United Kingdom, under the Accession Number NCIB 40087.]

Thus, it is probable 'pseudo-operator' sequences can be found in all genes. In general, then, a pseudo- operator is a DNA sequence present at a suitable position in a gene, including a plant gene, at which repressor binding will lead to inhibition of gene expression.

Thus, this invention also provides a selection system which permits the selection of altered specificity repressors exhibiting very broad specificities.

The present invention also provides the following plasmids which are suitable for use in performing the selection method of the invention: (i) The plasmid pAD18 which has been deposited, under the terms of the Budapest Treaty, in an *Escherichia coli*, strain DH5α, host, with The National Collections of Industrial and Marine Bacteria Limited, Aberdeen, United Kingdom, on Dec. 21, 1988, under the accession Number 40096. (ii) The plasmid pPS1 which has been deposited, under the terms of the Budapest Treaty, in an *Escherichia coli*, strain DH5α, host, with the National Collections of Industrial and Marine Bacteria Limited, Aberdeen, United Kingdom, on Dec. 21, 1988, under the accession Number 40097.

This invention is also applicable to protein molecules which lead to an increase in gene activity, particulary the selection of repressors/activator proteins which respond to specific chemicals. Binding domains for these chemicals can be selected and specifically manipulated to allow the generation of specific protein/DNA effect chemical combinations which are of use in biotechnology, for example as a chemical switch package enabling the controlled regulation of plant genes by application of an exogenous chemical inducer.

Mutations which affect both repressors and operators occur in vivo. It has been shown that repressors which have altered DNA recognition specificities can be engineered in vitro. The invention, then, depends on the ability of rare repressor mutants to switch off a conditionally lethal gene by binding at pseudo-operator sequences which the native repressor cannot recognise.

One embodiment of the invention will now be described, by way of illustration, in the following example, with reference to FIG. 1 which shows a map representing two series of plasmids designated pPS and pAD and variants.

EXAMPLE

Figures 1A, 1B:
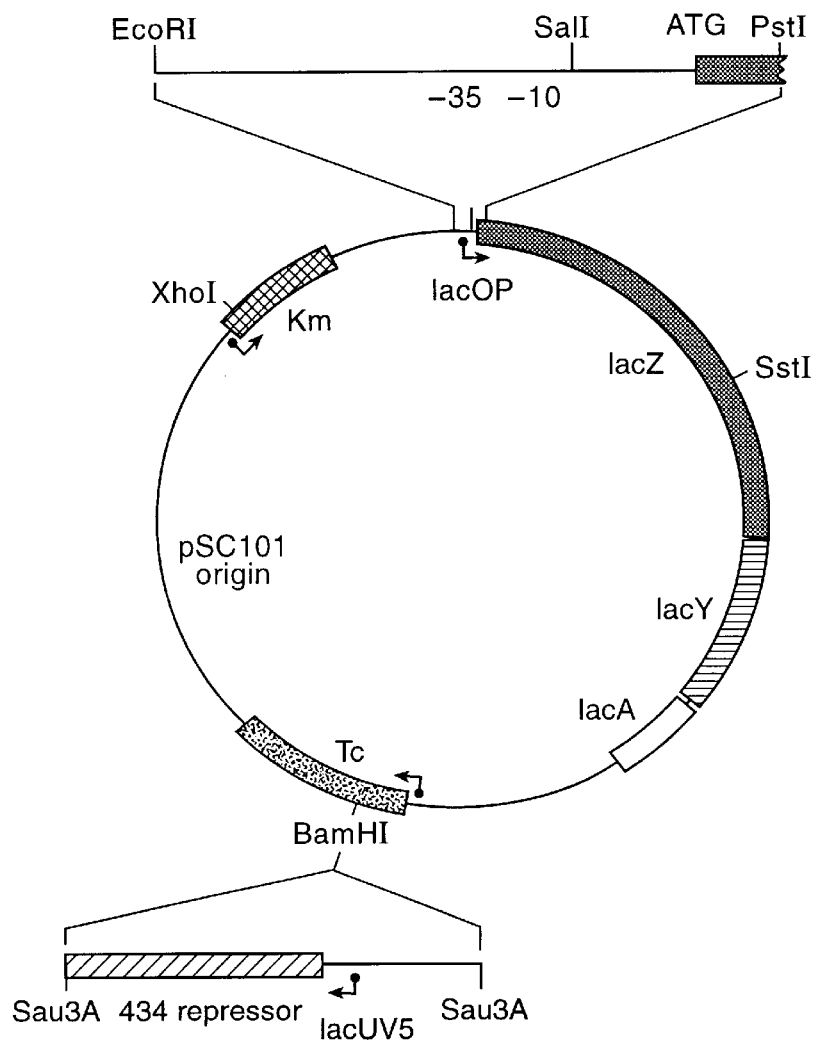
FIG. 1 shows a map representing two series of plasmids designated pPS and pAD and variants.

We demonstrate the selection system of the invention on repressor phage 434. However, in principle any other repressor can be adapted for this selection system.

1. The Selection System

We have designed a selection system that can be used for the selection of mutants in a wide range of repressor-operator systems. The selection system comprises a set of plasmids and the appropriate *E. coli* hosts, as well as a suicide substrate selection protocol adapted for the plasmids and hosts.

In its final form the system depends on the ability of rare repressor mutants to switch off a conditionally lethal gene through the binding at a 'pseudo-operator' which the wild type repressor cannot bind. The selection system described below contains features which maximise the frequency of such repressor mutants to be identified in the final population of cells.

The selection procedure is based on the lac operon of *Escherichia coli* and the use of the suicide substrate para-nitrophenyl-1-thio-β-D-galactoside (TPNPG). The lac operon (which contains the three genes lacZ, lacY and lacA) is controlled by the binding of LacI repressor to an operator sequence, lacO, situated between the transcription start site and the lacZ gene. The lacY gene product, lactose permease, is responsible for the active uptake of lactose and related compounds into the cytosol where they are hydrolysed by β-galactosidase (the lacZ gene product) to form galactose and glucose.

The positive selection system exploits the discovery that the growth of cells expressing the lacY gene is selectively inhibited in the presence of TONPG or TPNPG, presumably through the waste of metabolic energy on its transport. The selectivity of these compounds has been shown to be enhanced when succinate is used as the carbon source.

The rationale behind the selection is based on the ability of 434 repressor to bind the pseudo-operator sequences inserted in the promoter driving expression of the lac gene cassette. In the absence of a 434 repressor/operator complex, the lac operon will be expressed and, in the presence of TPNPG, will result in cell death. Conversely, in the presence of a complex, the LacY permease will not be expressed, and the suicide substrate TPNPG will be unable to enter the cell. Consequently, in the final analysis, a pseudo-operator chosen from the natural sequence of the target plant gene will be cloned into the SalI site and combined with a pool of genes encoding 434 repressors in which certain amino acids in the α3 helix are randomly substituted. Only those cells expressing mutant repressor that is able to bind the pseudo-operator, and consequently repress lacY expression, will be selected in the presence of TPNPG.

2. The Plasmids 2.1 Construction of pAD18 and Derivatives

A series of plasmids have been developed for use in these experiments. The prototype of these is pAD18, a map of which is shown in the Figure. This vector is based on a replicon from pSC101, which is known to be stably maintained in *E. coli*, and to have a low copy number. This is important as overexpression of DNA binding proteins may have deleterious effects on the growth of the host. If this is a problem in some experiments, it is advisable to transfer genes contained on the pAD18 to a bacteriophage vector for insertion into the bacterial genome as a single copy gene.

pAD18 has a kanamycin selectable marker for maintainance in *E. coli* strains.

pAD18 also contains the lac operon. The lacZ and lacY genes are present under the control of the lac promoter/operator. Into the lac operator, a SalI restriction site has been engineered which is used for insertion of the 434 operator, or in derivatives of pAD18, mutant 434 operators or selected 'pseudo-operators'. This site has been positioned in such a way that it will not interfere with expression of the lac operon from the lac promoter through steric hinderances when sufficient repressor is synthesised to bind to the operator cloned into that site. Those bases were changed into SalI restriction sites which are known not to be involved in contact with RNA polymerase. Thus the lac operon expression will be manipulated under the control of the 434 repressor. pAD18 which contains the wild-type 434 operator is thus the prototype of this series of plasmids.

pAD18 contains a tetracycline resistance gene, into which a wild type 434 repressor gene under the control of the lacUV5 promoter can be inserted for high level of expression. This vector is called pPS1. Further derivatives are described below.

In another vector, the 434 repressor has been modified such that a Kpn1 and Not1 site has been introduced at either side of the DNA binding helix whilst the native amino acid sequence in this region has been preserved. It is thus be possible to insert into this 434 repressor gene random oligonulceotides which when expressed will generate 434 repressor molecules which express altered DNA binding domains. The selection system using a suicide substrate will then permit the selection of those 434 mutant repressors which bind to the 'pseudo-operator'. In some circumstances this may also provide the selection pressure for isolation of repressor mutants. However, the system as it stands is dependent on expression/repression of the lacY permease for the isolation of repressor mutants.

Thus, there are convenient cloning sites in pAD18 and its derivatives for insertion of operators or repressor genes. Operators can be cloned into precursor vectors of pAD18, especially pRW283, from which the operator containing EcoR1 to Pst1 fragment can subsequently be excised and cloned into EcoR1 and Pst1 digested pAD18 (see FIG. 1).

One objective was to show that the expression of the lac operon carried by the plasmids described above could be controlled by 434 repressor/operator interactions. To demonstrate this, three plasmids were constructed in which the 434 operators carried by pAD16, 17 and 18 were combined with the wild-type 434cI gene on pAD15.2. The large XhoI/SstI fragment (9.4 kb) from pAD15.2 was purified and ligated to the small XhoI/SstI fragment (3.7 kb) purified from pAD16, 17 and 18 to form plasmids pPS2, pPS3 and pPS1, respectively. Restriction analysis of plasmid DNA isolated from several transformants from each ligation showed that all pPS plasmids had the expected overall structure. The structure of these plasmids is shown in FIG. 1.

The integrity of the operators carried by the pAD and pPS plasmids was checked by sequencing. Initially this was achieved by isolating the approximately 200 base-pair EcoRI/PstI fragment, which carries the whole of the lac promoter and the 5' end of the lacZ gene, from each of the pAD and pPS plasmids and subcloning them into the polylinker of M13mpl8. Single-stranded template was purified and sequenced according to standard protocols. Alternatively, this laborious subcloning procedure was circumvented by using plasmid sequencing. These analyses showed that the appropriate 14 mer operator sequence was present at the SalI site in all relevant plasmids. The presence of other salient features of the lac promoter was also confirmed.

2.2 pPS Plasmids Encode Functional 434 Repressor

To visualise the 434 repressor produced by pAD15.2 and the pPS plasmids, total protein extracts were prepared from mid-log cultures grown under selective conditions. Following polyacrylamide gel electrophoresis and Coomassie brilliant blue (G250) staining, no proteins corresponding to the size of the repressor could be observed specifically in strains containing the 434cI gene. However, other experiments have shown that 1 $\mu$g of purified repressor is only just visible using this relatively insensitive technique. Therefore, to detect 434 repressor in the amount of extract used an expression level of at least 1% total cell protein would be required. The background of other similar-sized proteins also makes detection difficult. Consequently, the much more sensitive Western blotting technique was used.

The primary antibody required to detect 434 repressor by Western blotting was prepared by injecting rabbits with purified intact 434 repressor. The specificity of this polyclonal antiserum was demonstrated using purified repressor and extracts of E.coli strains harbouring the 434cI gene. At low dilutions of antiserum several proteins from bacterial extracts, including 434 repressor, were detected. However, further dilution of the antiserum resulted in only 434 repressor remaining detectable, the maximum specificity being observed at dilutions of 1/10000 to 1/20000.

The sensitivity of Western blotting using this antibody preparation and the horse-radish peroxidase conjugate detection technique was assessed by "spiking" crude cell extracts of 6300Δlac4169, which contains no 434cI gene, with various amounts of the purified repressor. Under standard conditions, 5ng of repressor in 50 $\mu$g of extract could readily be detected, this sensitivity corresponding to an expression level of 0.01% total cell protein.

Use of the same primary antibody in Western blots of 6300Δlac4169 strains carrying the test plasmids showed conclusively that cells harbouring pAD15.2, pPS1, pPS2 and pPS3 all synthesised 434 repressor. Determination of the relative intensities of the bands obtained, using a scanning densitometer, showed that all four strains contain approximately 0.4% total cell protein as 434 repressor.

Finally, the ability of the 434 repressor to bind wild-type operator sequences was determined in a functional assay using bacteriophage 434cI, 434vir and λcI. In the life cycle of these phage, the binding of the appropriate repressor to operators within the promoter $P_R$ represses transcription of the genes responsible for cell lysis. Consequently, cells which endogenously synthesise cI repressor are immune to lysis by the corresponding phage due to the inhibition of lytic gene expression by the already existing repressor. Since the cI mutant phage are unable to synthesise repressor, the lytic phenotype after infection by these phage is diagnostic for the absence of repressor in the host cell. The $P_R$ operators of vir mutant phage have a reduced affinity for repressor, with the consequence that at low levels of endogenous repressor this phage is lytic, whereas at higher repressor concentrations super-infection is inhibited.

The results of cross-streaking these phage with the test strains show that cells harbouring the pPS plasmids are immune to super-infection by both 434cI and 434vir, but are sensitive to λcI. Strains carrying other pAD plasmids were sensitive to all three phage. This clearly indicates that cells carrying the pPS plasmids synthesise high levels of 434 repressor that is functionally able to bind operator and inhibit transcription from $P_R$. Furthermore, the specificity of this repressor/operator interaction is demonstrated by the inability of 434 repressor to bind the operators of λcI, which have a different sequence to those of 434, resulting in cell lysis.

In summary, all three pPS plasmids were determined to be of the correct construction, to carry the expected 434 operator sequence and to synthesise functional 434 repressor.

2.3 Vector Improvement

As indicated below, a proportion of the population of pAD and pPS plasmid-containing strains form white colonies upon selection. Furthermore, it has been observed that if strains containing these plasmids are kept on selective media for several months, sub-culturing when necessary, the proportion of white colonies in the population increases.

It is presumed that these white colonies carry plasmids in which part of all of the lac operon is mutated or deleted. The usual method of minimising such problems is to use a recombination-deficient strain. However, the combination of the Δlac4169 and recA56 alleles renders the strain inviable in the presence of TPNPG, the reason for this being unclear. Therefore, attention has turned to the probable source of the recombinatory events. It is noted that the promoters expressing the lac operon and the 434 repressor gene in the pPS plasmids are both derived from the lac promoter and consequently the sequences are very similar. Recombination between these sequences would result in the deletion of the lac operon, given that the origin sequences and the kanamycin-resistance gene must remain under the selective conditions imposed.

During the construction of pAD15.2, the 434cI gene was transferred from plasmid pRP42 on a 1 kb Sau3A fragment. The stop codon of the 434 repressor reading frame coincides with the Sau3A site at the right hand side of this fragment, consequently the gene cloned into pAD15.2 carries no transcriptional termination signals. Furthermore, this Sau3A fragment also carries a remnant of pBR322, including the ampicillin-resistance gene promoter. Therefore, to rectify these problems sequences both upstream and downstream of the 434cI coding sequence were altered. The region upstream was replaced with the tryptophan promoter and a consensus Shine-Dalgarno sequence using appropriate oligonucleotides. This both prevents intra-plasmidic recombination and removes the ampicillin-resistance gene promoter.

The rrn T1 terminator was also introduced at the 3' end of the 434cI coding sequence to terminate the 434cI gene transcripts. This rho-independent terminator was chosen since its reported bi-directional termination activity would avoid any disruption of 434cI expression from opposing transcripts initiated elsewhere in the vector as well as terminating 434cI transcripts.

2.4 Construction of Plasmid pTP1 oligonucleotides were used to introduce the wild-type trp promoter sequence together with the consensus Shine-Dalgarno sequence (AGGAGGT) 5 base-pairs upstream of the 434cI gene translational start site. This spacing gives maximal translational activity of the 434cI gene. Due to the lack of convenient restriction sites at the start of the 434cI gene, the EcoRI site 33 base-pairs inside the coding sequence was used. This necessitated the inclusion of the 5' end of the coding region in the oligonucleotide. The required sequence is 126 base-pairs long and thus was constructed from four overlapping oligonucleotides. Following the annealling of these oligonucleotides, the duplex 126 base-pair fragment was isolated and cloned into EcoRI-cleaved pUC19 vector. Following the selection of transformants on media containing ampicillin and BCIG, DNA from several white colonies was sequenced using plasmid sequencing protocols. This confirmed the structure of the promoter sequence to be as expected.

2.5 Construction of pTT1

The sequence of the rrn T1 terminator has a long G≡C rich stem structure flanked by long A=T rich regions making it a strong terminator for transcripts in both orientations. Due to the inverted repeat nature of this sequence, it was inserted using four oligonucleotides thereby avoiding any problems of self-annealling within each strand. The oligonucleotides were annealled pairwise and the resultant double-stranded DNAs isolated separately and ligated to EcoRI/HindIII cleaved pTP1 DNA, prior to transformation of cells to ampicillin-resistance. The sequence of the inserted terminator structure was ascertained.

2.6 Construction of Plasmid pTRT1

The source of the 434cI gene to be cloned behind the trp promoter was plasmid pRP42-76. Silent mutations have been introduced, using in vitro mutagenesis, to create restriction sites for KpnI and XmaIII on either side of the sequence coding for the α3 recognition helix. This will subsequently allow the introduction of oligonucleotides in which certain codons in the α3 helix have been randomly mutated. The EcoRI/Sau3A fragment (approx. 600 basepairs) carrying the 434cI gene was isolated and cloned into EcoRI/BglII cleaved pTP1. This reforms the 434cI open reading frame exactly and the translational stop codon is retained within the Sau3A/BglII junction. Once isolated, the trpP-434cI-rrnT1 cassette was cleaved out using the BamHI sites in the polylinkers introduced at either end of the cassette and used to replace the existing 434cI gene in the pAD and pPS plasmids.

The sequence of the trp promoter used to construct pTRT1 is bound by trp repressor in the presence of tryptophan to inhibit transcription. The binding site for this repressor was intentionally retained in order that expression of the 434cI gene may be controlled, if necessary, in future work. However, in order to conveniently allow the synthesis of 434 repressor, strains will be constructed in which the trpR gene has been deleted from the chromosome.

3. Selection Protocol
3.1 Selection using TONPG

A TONPG (ortho-nitrophenyl-b-thiogalactoside) selection protocol was designed which allows selection for clones in which a mutant repressor now binds to the mutant 434 operator resulting in repression of lacY expression (i.e. selection by repression of conditional inhibition).

TONPG inhibits the growth of *E. coli* cells that are expressing the lacY permease gene. Early work with single copy lacY+ *E. coli* indicated that these cells were maximally sensitive to TONPG at 500 to 1000 micrograms/ml when expressing lacY in succinate minimal medium. Mixing experiments showed that TONPG could be used to select lacY cells from a mixed lacY+/− population. These experiments were repeated with lacY+ and lacY− pAD plasmids. The TONPG selection will only work in a lac-deleted *E. coli* host. The preferred host is described below. Selection works better in liquid cultures, but also works on agar plates. Selection on solid medium works better with a different galactoside analogue-para-nitrophenyl-beta-thiogalactoside (TPNPG). Using TONPG in liquid cultures and TPNPG in plates, the selection normally achieves a 6 log enrichment of lac-pAD plasmids present in the initial population.

3.2 The *E.coli* host

The bacterial host selected was such as to enable selection by TONPG. This required the ability of the host to grow in a succinate minimal medium. The particular host used in this Example was one from which the entire lac operon had been deleted, lacΔ4129. However, other suitable mutants hosts can be used, for example laci⁻, lacY⁻. A suitable strain was constructed from strain W1485 (CGSC6300) derivative which was deleted for the entire lac operon, using transposon-linked P1 transduction.

3.3 Selection using TPNPG

To test the ability of TPNPG to select lac⁻ cells from a background of lac⁺ cells, mixing experiments with cultures of 6300lac⁺ and its Δlac4169 derivative were performed. These strains were grown to mid-log phase in the presence of 1 mM IPTG, to induce expression of the lactose operon. The two cultures were mixed in various proportions before plating suitable dilutions on minimal-salts-succinate plates containing 1 mM IPTG and 50 μg/l BCIG, both with and without TPNPG.

Initial experiments showed that 500 μg/ml TPNPG was only able to retard the growth of lac⁺ cells, allowing the formation of small blue colonies after 48 h at 28° C. However, this background was eliminated in the presence of 1 mg/ml TPNPG, resulting in none of the lac⁺ cells plated (up to 7× 10⁻⁷) being able to form blue colonies (Table I). In contrast, this TPNPG concentration did not noticeably affect the viability of the lac⁻ cells. This demonstrates the high selective power of TPNPG againstlac⁺ cells, even when the lacY gene is chromosomal and thus at a low copy number. In this respect, the higher copy number and therefore increased expression level of the lac genes on the pPS plasmids should result in a greater waste of energy on TPNPG uptake, making the killing of lac⁺ cells more effective.

TABLE I

ABILITY OF TPNPG TO SELECT LAC− CELLS FROM A BACKGROUND OF LAC+ CELLS

| Approx. ratio of cells plated | Colonies formed/ml | | | |
|---|---|---|---|---|
| | −TONPG | | +TONPG | |
| lac−: lac+ | White | Blue | White | Blue |
| 1:10² | 1.1 × 10² | 2.0 × 10⁴ | 1.2 × 10² | 0 |
| 1:10³ | 1.3 × 10² | 2.0 × 10⁵ | 1.2 × 10² | 0 |
| 1:10⁴ | N.D. | 1.8 × 10⁶ | 1.1 × 10² | 0 |
| 1:10⁵ | N.D. | 1.5 × 10⁷ | 1.1 × 10² | 0 |
| 1:5 × 10⁵ | N.D. | 7.0 × 10⁷ | 1.2 × 10² | 0 |

N.D. = Not Determinable

The effect of TPNPG on the survival of 6300Δlac4169 cells carrying various pAD and pPS plasmids was tested by plating appropriate dilutions of cultures on the media as described above. The results from two experiments revealed that all plasmids resulted in the formation of both blue and white colonies in the presence of TPNPG, yet no white colonies were detected in its absence (Table 2).

TABLE 2

| Plasmid carried | Colonies/ml | | | |
|---|---|---|---|---|
| | −TPNPG | | +TPNPG | |
| | White | Blue | White | Blue |
| Expt #1 | | | | |
| — | 2.8 × 10⁸ | 0 | 3.0 × 10⁸ | 0 |
| pAD16 | ND | 3.5 × 10⁸ | 1.2 × 10³ | 2.0 × 10³ |
| pAD17 | ND | 2.3 × 10⁸ | 1.3 × 10⁴ | 1.6 × 10³ |
| pAD18 | ND | 2.3 × 10⁸ | 2.3 × 10³ | 2.2 × 10³ |
| pPS1 | ND | 3.8 × 10⁷ | 2.0 × 10⁴ | 2.7 × 10⁷ |
| pPS2 | ND | 7.2 × 10⁷ | 7.0 × 10² | 4.8 × 10⁷ |
| pPS3 | ND | 5.6 × 10⁶ | 2.0 × 10⁴ | 2.0 × 10¹ |
| Expt #2 | | | | |
| — | 3.1 × 10⁸ | 0 | 3.0 × 10⁸ | 0 |
| pAD16 | ND | 2.9 × 10⁸ | 1.1 × 10⁴ | 4.2 × 10² |
| pAD17 | ND | 3.4 × 10⁸ | 6.7 × 10³ | 5.9 × 10³ |
| pAD18 | ND | 2.7 × 10⁸ | 4.1 × 10³ | 2.5 × 10³ |
| pPS1 | ND | 4.2 × 10⁷ | 8.5 × 10³ | 1.2 × 10⁷ |
| pPS2 | ND | 8.4 × 10⁷ | 5.2 × 10³ | 1.6 × 10⁷ |
| pPS3 | ND | 5.8 × 10⁷ | 5.7 × 10³ | 6.3 × 10¹ |

ND = Not Determinable

As already observed, all pAD and pPS plasmids give blue colonies on media containing BCIG, irrespective of the presence of 434 repressor/operator interactions. Presumably therefore, the white colonies formed must result from cells carrying plasmids which have been mutated or deleted to render the cell effectively lac⁻. The relatively low frequency with which these white colonies occur (approx. $10^{-5}$ of cells plated) suggests that, on media lacking TPNPG, they would remain undetected amongst the majority of blue colonies. Analysis of the plasmids harboured by cells of such white colonies revealed deletions (see above).

In the presence of TPNPG the frequency of blue colonies formed by pAD-carrying strains was reduced by $10^5$ to $10^6$. This represents the killing by TPNPG of the majority of the population harbouring an un-repressed lac operon. The strain carrying pPS3 was also killed to a similar extent in the presence of TPNPG, as would be expected given that it has already been shown that the 434 repressor is incapable of inhibiting transcription of the lac genes in this plasmid. However, in all cases, a residual number of blue colonies were obtained in the presence of TPNPG, at a frequency of approximately $10^{-5}$ of the cells plated. It is presumed that these colonies primarily represent cells harbouring lacy⁻ mutant plasmids, since it has already been demonstrated that the selective power of TPNPG is sufficient to kill the vast majority of the cells plated, given that they all remain lac⁺. Since previous experiments have not indicated a high mutation frequency for the chromosomally borne lacY gene (Table I), it is presumed that intra-plasmidic recombination is responsible for the apparently high number of mutants. Previous work has indicated that these plasmids are prone to instability in rec⁺ strains and that a 6300Δlac4169 recA56 strain, which could be used to prevent such recombination, is inviable on TPNPG.

However, in sharp contrast to the other strains, the vast majority of cells containing pPS1 or pPS2 survive in the presence of TPNPG, the number of blue colonies being reduced by only 2–5 fold, this reduction being least-for pPS1. This clearly correlates with the emphatic reduction in β-galactosidase activity, and therefore also presumably lacY expression, already demonstrated for these plasmids. Therefore, the important conclusion can be drawn that the interaction between 434 repressor and its cognate operator is able to reduce lac gene expression sufficiently to allow the majority of cells to survive the selective procedure.

4. Selection of Altered Specificity Repressors 4(a) Selection of Altered 434 Repressor A 434 gene which had been altered to facilitate random mutagenesis of the 434 repressor binding domain through insertion of random oligonucleotides has been described (Wharton and Ptashane, Nature 316, 601–605). The 434 repressor gene has been mutagenized to introduce KpnI and NotI restriction enzyme cleavage sites on either side of the DNA recognition helix, whilst conserving the native amino acid sequence. Batches of oligonucleotides have been synthesised with the correct cohesive ends and containing varying frequencies of mutations randomly distributed throughout the DNA recognition alpha helix. These oligo mixtures have been cloned between the KpnI and the NotI cohesive ends of the modified 434 repressor gene. Alternatively the 'dirty oligo' approach has been used for the generation of mixed oligo with base substitutions at appropriate positions of the DNA binding domain.

4(b) Selection of Altered 434 Repressor Recognising Pseudo-Operator found in Plant Genes A naturally occurring pseudo-operator was used for the selection of altered repressor. The target for this work was the GPAL2 gene from French bean, the chlorophyll a/b binding protein gene from maize, and others. We have identified by computer analysis, that several potential 434 pseudo-operators are located in the region of the GPAL2 gene. These regions of the GPAL2 promoter were used to select an altered specificity 434 repressor. The 'pseudo-opertor' sequences were inserted into the −10 to −35 region of the lac promoter driving the lacz/lacY genes. Dirty oligo's were inserted into the 434 repressor gene and mixtures were transformed into *E.coli* 6300. The selection protocol was applied and colonies isolated. Using microbiological and molelcular techniques we have demonstrated that mutant repressors can be selected for. The characterisation of the repressor gene has been done by DNA sequence analysis, and binding studies to determine the strength of the repressor binding.

In summary, then, the present invention provides a selection system comprising preferably of bacterial strains and plasmids, and a sensitive suicide substrate selection protocol. This selection system can be used to select altered specificty repressors. Implied in this invention is the provision of controlling gene expression in organisms by said altered- specificity repressors. The only requirement for this method of control of gene expression are the DNA sequence of the target gene, the identification of 'pseudo-operators' being a DNA sequence that resembles the normal operator sequence and a selection system which permits the selection of repressors capable of binding to said 'pseudo-operators'.

We claim:

1. A method of regulating a target gene in a target eukaryotic genome by pseudo-operator/repressor interaction comprising:
   (a) identifying said pseudo-operator as a DNA sequence which is upstream of said target gene and has overall dyad symmetry of an operator;
   (b) transforming a bacterial host with a recombinant plasmid which contains
      (i) said pseudo-operator operatively linked to a marker gene and controlling expression thereof, and
      (ii) a gene encoding a potential bacterial repressor for said pseudo-operator;
   (c) selecting a culture of transformants, wherein said repressor is identified by repression of marker gene expression in the bacterial host by positive selection for said repression of marker gene expression; and
   (d) transforming said target eukaryotic genome with a gene encoding said selected repressor, wherein said selected repressor gene is capable of regulating said target gene.

2. A method of regulating a target gene in a target genome by pseudo-operator/repressor interaction comprising:
   (a) identifying said pseudo-operator as a DNA sequence which is upstream of said target gene and has overall dyad symmetry of an operator;
   (b) transforming a bacterial host with a recombinant plasmid which contains
      (i) said pseudo-operator operatively linked to a marker gene and controlling expression thereof, and
      (ii) a gene encoding a potential bacterial repressor for said pseudo-operator;
   (c) selecting a culture of transformants, wherein said repressor is identified by repression of marker gene expression in the bacterial host by positive selection for said repression of marker gene expression; and
   (d) transforming said target genome with a gene encoding said selected repressor, wherein said selected repressor gene is capable of regulating said target gene; in which said recombinant plasmid contains an *Escherichia coli* lac operon; said pseudo-operator controls expression of the lac operon; and said culture of transformants is selected in the presence of ortho- or para-nitro-phenyl-1-thio-β-galactoside, thereby inhibiting growth of transformants in which expression of the lac operon is not repressed by said repressor and not inhibiting growth of transformants in which repression occurs.

3. A method as claimed in claim 2 in which said pseudo-operator is obtained from a eukaryotic DNA sequence.

4. A method as claimed in claim 1 or claim 2 in which said repressor is encoded by a mutant gene.

5. A method as claimed in claim 4 in which said pseudo-operator is obtained from a plant DNA sequence and said target genome is a plant genome.

6. A method as claimed in claim 5 in which the bacterial host is *Escherichia coli*.

7. A method as claimed in claim 4 in which the bacterial host is *Escherichia coli*.

8. A method as claimed in claim 1 or claim 2 in which said pseudo-operator is obtained from a plant DNA sequence and said target genome is a plant genome.

9. A method as claimed in claim 8 in which the bacterial host is *Escherichia coli*.

10. A method as claimed in claim 1 or claim 2 in which the bacterial host is *Escherichia coli*.

11. A plant having expression system comprising:
 a DNA sequence which possesses overall dyad symmetry of a pseudo-operator upstream of a target plant gene, and controlling expression thereof; and further comprised of
 a gene encoding a repressor for said pseudo-operator selected by (a) to (c) of claim 1, wherein the selected repressor is capable of regulating target gene expression in plant cells by binding to said pseudo-operator.

12. A plant according to claim 11 wherein the selected repressor is stably integrated into the plant's genomic DNA.

13. The plasmid pAD18, which has been deposited, in an *Escherichia coli* DH5a host, with The National Collections of Industrial and Marine Bacteria Limited, Aberdeen, United Kingdom, on Dec. 21, 1988, under the Accession Number 40096, and variants thereof as set forth in FIG. 1.

14. The plasmid pPS1, which has been deposited, in an *Escherichia coli* DH5a host, with The National Collections of Industrial and Marine Bacteria Limited, Aberdeen, United Kingdom, on Dec. 21, 1988, under the Accession Number 40097, and variants thereof as set forth in FIG. 1.

* * * * *